(12) United States Patent
Rix et al.

(10) Patent No.: US 7,399,892 B2
(45) Date of Patent: Jul. 15, 2008

(54) PROCESS FOR DEWATERING ETHANOL (75) Inventors: Armin Rix, Marl (DE); Frank Höper, Haltern am See (DE); Jochen Praefke, Oer-Erkenschwick (DE); Wilfried Büschken, Haltern am See (DE)

(73) Assignee: OXENO Olefinchemie GmbH, Marl (DE)

( * ) Notice: Subject to any disclaimer, the term of this patent is extended or adjusted under 35 U.S.C. 154(b) by 0 days.

(21) Appl. No.: 11/624,823

(22) Filed: Jan. 19, 2007

(65) Prior Publication Data
US 2007/0173670 A1    Jul. 26, 2007

(30) Foreign Application Priority Data
Jan. 25, 2006   (DE) .................. 10 2006 003 492

(51) Int. Cl.
C07C 29/76    (2006.01)
C07C 29/74    (2006.01)

(52) U.S. Cl. ........................ 568/917; 568/913
(58) Field of Classification Search .............. 568/917, 568/913
See application file for complete search history.

(56) References Cited

U.S. PATENT DOCUMENTS

| 5,607,557 A | 3/1997 | Streicher |
| 6,107,526 A | 8/2000 | Frey et al. |
| 6,657,090 B2 | 12/2003 | Rix et al. |
| 7,002,053 B2 | 2/2006 | Nierlich et al. |
| 2006/0264681 A1 | 11/2006 | Obenaus et al. |

FOREIGN PATENT DOCUMENTS

EP    0 071 032 A1    2/1983

OTHER PUBLICATIONS

U.S. Appl. No. 11/624,823, filed Jan. 19, 2007, Rix et al.
U.S. Appl. No. 11/521,460, filed Sep. 15, 2006, Rix et al.
U.S. Appl. No. 11/614,275, Dec. 21, 2006, Praefke et al.
U.S. Appl. No. 11/610,801, filed Dec. 14, 2006, Fernandez et al.
A.H. Ballweg, et al. "Pervaporation Membranes-an Economical Method to Replace Conventional Dehydration and Rectification Columns in Ethanol Distilleries", Proceedings Fifth International Alcohol Fuel Technology Symposium, XP-009086757, vol. 1, May 1982, pp. 97-106.

*Primary Examiner*—Elvis O Price
(74) *Attorney, Agent, or Firm*—Oblon, Spivak, McClelland, Maier & Neustadt, P.C.

(57) ABSTRACT

A process for preparing low-water ethanol from at least two streams of relatively water-rich ethanol that have a different water content by dewatering at membranes. The low-water ethanol can be used to prepare ethyl tert-butyl ether (ETBE).

17 Claims, 2 Drawing Sheets

PROCESS FOR DEWATERING ETHANOL

REFERENCE TO RELATED APPLICATION

This application is based on German patent application 102006003492.9 filed Jan. 25, 2006, the contents of which are incorporated by reference herein.

FIELD OF THE INVENTION

The present invention relates to a process for dewatering ethanol, in particular for dewatering ethanol that is used to prepare ethyl tert-butyl ether (ETBE) by reacting ethanol with an isobutenic hydrocarbon mixture. The ethanol to be dewatered may stem partly from an ethanolic $C_4$ hydrocarbon stream obtained in an ETBE process.

BACKGROUND OF THE INVENTION

ETBE is a component for increasing the octane number in fuels for gasoline engines. ETBE is increasingly being used as an octane number improver in place of MTBE, because there is discussion about the use of MTBE in fuels due to possible groundwater contamination. In addition, the use of ETBE is required in some countries, for example Germany, when bioalcohol, i.e. ethanol, prepared from renewable raw materials (plants) is used to prepare ETBE.

ETBE can be obtained from $C_4$ olefin mixtures, for example from $C_4$ cuts from steamcrackers. These mixtures consist substantially of butadiene, the monoolefins, isobutene, 1-butene and the two 2-butenes, and also the saturated hydrocarbons isobutane and n-butane. Customary workup processes practiced worldwide for such $C_4$ cuts include the following steps. First, the majority of the butadiene is removed. When butadiene can be brought to market viably or there is in-house consumption, it is removed, for example, by extraction or extractive distillation. Otherwise, the butadiene is hydrogenated selectively to linear butenes to as full an extent as possible, but at least up to concentrations of from 1 to 0.1% by mass. In both cases, a hydrocarbon mixture (frequently referred to as raffinate I or hydrogenated crack-$C_4$) remains, which, in addition to the saturated hydrocarbons (n-butane and isobutane), includes the olefins (isobutene, 1-butene and 2-butenes). The isobutene present therein is reacted with ethanol to give ETBE. The distillative workup gives rise to ETBE and an ethanolic $C_4$ hydrocarbon mixture from which ethanol is removed by extraction with water.

In industry, isobutene or isobutenic hydrocarbon streams are usually reacted over solid acidic catalysts, for example, over acidic ion exchange resins.

In this reaction, water reduces the activity of the catalyst very greatly and thus lowers the space-time yield for ETBE. In addition, isobutene in the presence of water forms tert-butanol (TBA) as a by-product. In industry, low-water ethanols are therefore used in the preparation of ETBE, especially those that have a water content of below 1% by mass.

The commercial ethanol qualities have a water content of from 5 to less than 1% by mass. The homoazeotrope of ethanol and water still has a water content of 4.4% by mass. Drier ethanols, especially those having a water content of below 1% by mass, can be prepared only at a high level of cost and inconveniently.

An industrial process for dewatering ethanol is azeotropic distillation with an azeotroping agent that forms a ternary minimum heteroazeotrope with ethanol and water. The azeotroping agents used are, for example, heptane, cyclohexane or benzene. A general flow diagram of such a plant and literature references can be found in Ullmann's Encyclopedia of Technical Chemistry, Vol. 9, pages 634-635, $5^{th}$ Edition. The main disadvantage of these dewatering processes lies in their high operating costs.

A further process for drying ethanol is water removal by pervaporation at membranes (for example, U. Sander, H. Janssen, Industrial application of vapour permeation, Journal of Membrane Science, 61 (1991), p. 113 to 129, Elsevier Science Publishers B. V, Amsterdam; A. H. Ballweg, H. E. A. Brüschke, W. H. Schneider, G. F. Tusel, Pervaporation Membranes, Proceedings of Fifth International Alcohol Fuel Technology 1982, p. 97 to 106; H. E. A. Brüschke, State of Art of Pervaporation, Proceeding of Third International Conference on Pervaporation 1988, p. 2 to 11). In this process, the water to be removed is obtained together with ethanol in vapor form as the permeate. In order to achieve maximum water removal, the pervaporation is carried out in a plurality of membrane modules connected in series, the retentate of one module in each case being the use mixture of the next module. This process is suitable particularly for the dewatering of ethanols with a very low water content (from 1 to 10% by mass). The permeates obtained can be worked up in a column to give the ethanol/water azeotrope which can be recycled into a membrane unit. The main disadvantage of this process lies in the high capital investment for the membrane modules.

In most ETBE plants, there are typically at least two different ethanol streams, specifically the use ethanol (ethanol from another plant or bought-in material) and at least one ethanol stream recovered from an ethanolic $C_4$ mixture by extraction and distillation. The fresh ethanol generally has a water content of from greater than 0 to less than 1 to approx. 5% by mass; the recovered ethanol usually has a water content of from 5 to 12% by mass. Typically, these streams are combined before dewatering.

OBJECT OF THE INVENTION

It is an object of the present invention to provide an alternative process for the dewatering of two ethanol streams with different water content, which preferably avoids the disadvantages of the known dewatering processes in which the two ethanol streams are mixed before the dewatering.

BRIEF DESCRIPTION OF THE INVENTION

It has now been found that, surprisingly, the membrane surface that is needed for the removal of the water from the two ethanol streams can be reduced when the two streams with different water content are worked up in separate membrane units optimized for the individual feed concentration. The secondary units (condensation, coolant circulation, vacuum generation) may optionally be utilized by the two membrane units together.

The present invention therefore provides a process for preparing relatively low-water ethanol from at least two streams of relatively water-rich ethanol that have a different water content by dewatering using membranes. In the process, ethanol streams with different water contents are introduced separately into different membrane units in which the ethanol streams are each separated into relatively low-water ethanol as the retentate and relatively water-rich permeate. Then the retentate stream from at least one membrane unit for drying an ethanol stream with a relatively high water content is combined with the feed stream and/or the retentate stream of at least one other membrane unit for drying an ethanol stream;

only streams that have a difference in the ethanol concentration of not more than 1% by mass absolute are combined.

The present invention likewise provides a composition of ethanol and water having a water content of less than 1% by mass, that has been prepared by the process according to the invention.

The present invention also provides for the use of compositions comprising ethanol, prepared by the process according to the invention, as a reactant for preparing ETBE.

Moreover, the invention can be utilized for dewatering only one ethanol stream, in which case the ethanol/water mixture obtained by distillative workup of the permeates obtained in the separation constitutes the second ethanol stream in a formal sense.

The present invention has the advantage that the reduction in the membrane surfaces needed for the water removal allows capital investment to be lowered, and reduction in the membrane surface to be replaced regularly also allows operating costs to be lowered.

DETAILED DESCRIPTION OF THE INVENTION

The process according to the invention will be described by way of example hereinafter, without any intention that the invention, its scope of protection that is evident from the claims and the overall description, be restricted thereto. The claims themselves too are included in the disclosure content of the present invention. When ranges or preferred ranges are specified in the text below, all theoretically possible intermediate ranges and individual values lying within these ranges shall be included in the disclosure content of the present invention without this having been stated explicitly for reasons of better clarity.

In the process according to the invention for preparing relatively low-water ethanol from at least two streams of relatively water-rich ethanol that have a different water content by dewatering at membranes, the ethanol streams with different water contents are introduced separately into different membrane units in which the ethanol streams are each separated into relatively low-water ethanol as the retentate and relatively water-rich permeate, and the retentate stream from at least one membrane unit for separating an ethanol stream having a relatively high water content is combined with the feed stream and/or the retentate stream of at least one other membrane unit for separating an ethanol stream, only streams which have a difference in the ethanol concentration of not more than 1% by mass absolute being combined.

Preferably, only those retentate streams that have a difference in the absolute ethanol concentration of not more than 0.5% by mass, preferably of not more than 0.2% by mass and most preferably of from 0 to 0.2% by mass, in particular from 0.001 to 0.1% by mass, are combined with feed streams and/or retentate streams of other membrane units. Only when the difference in the water concentration of the two streams to be combined becomes less than 1% by mass can the advantages of separate workup no longer sufficiently balance out the higher capital costs, so that a combined workup is then preferred.

It may be advantageous when the retentate stream from at least one membrane unit for separating an ethanol stream having a relatively high water content is combined with the feed stream and/or the retentate stream of at least one membrane unit for separating an ethanol stream with a relatively low water content. Preferably, two water-rich ethanol streams with different water contents are present, so that the retentate from the membrane unit in which the ethanol stream with the relatively high water content is dewatered can be combined with the feed stream to and/or the retentate stream from the membrane unit in which the ethanol stream with the relatively low water content is dewatered. In the context of the present invention, relatively low-water ethanol is understood in particular to mean ethanol or a composition comprising ethanol that has a water content that is less than the water content of the relatively water-rich streams of ethanol and that more preferably has a water content that is less than the water content of the ethanol/water azeotrope at standard pressure.

In the context of the present invention, the term membrane unit means at least one membrane or a unit having a membrane module. A membrane unit may, for example, have a membrane module or a plurality of membrane modules connected in series or parallel or an arrangement of membrane modules connected in parallel and in series. The membrane modules used may be commercial modules. In the membrane modules, one or more membranes may be present.

The at least two relatively water-rich ethanol streams that are used in the process according to the invention and have different water contents differ in their water concentration preferably by more than 1% by mass absolute, preferably by from 1.1 to 10% by mass absolute and more preferably by from 2 to 5% by mass absolute. The relatively water-rich ethanol streams may, for example, be ethanol from ethanol production, for example, from bioethanol production or industrial ethanol production. In the case of these fresh alcohols, the different water content may result, for example, from a different preparation process. In the case of the water-rich streams, they may also be recycle streams as can occur in processes in which ethanol is used as the reactant. The relatively water-rich ethanol streams may also be one or more fresh alcohol streams and one or more recycle streams. Because the process according to the invention is suitable in particular for working up ethanol streams to be used in ETBE syntheses or processes, the relatively water-rich ethanol streams used in the process according to the invention are preferably fresh alcohol and at least one water-rich ethanol stream that stems from an ETBE plant or an ETBE process.

In the process according to the invention, water can be removed from the relatively water-rich ethanol streams by reverse osmosis (liquid feed and liquid retentate; liquid permeate), vapor permeation (vapor input stream and retentate; vaporous permeate) or by pervaporation (liquid input stream and liquid retentate; vaporous permeate). Moreover, a removal by simultaneous pervaporation and vapor permeation is also possible. Particular preference is given to effecting the removal by pervaporation. In the process according to the invention, it is possible that two or more of the membrane units present work by a different separation principle or the same separation principle. Preference is given to using the same separation principle, i.e. in particular pervaporation, in all membrane units.

In the process according to the invention, it is possible to use commercial, preferably hydrophilic membranes. The membranes may, for example, be polymer membranes or inorganic membranes or else composite membranes that have both inorganic and organic materials. In the process according to the invention, it is possible to use, for example, polymer membranes from Sulzer Chemtech, CM-Celfa, GKSS or Sophisticated Systems (polyimide membrane), for example Pervap 2200, Pervap 2201, Pervap 2256, Pervap 2510 from Sulzer, or 2SDP-H018 from Sophisticated Systems. The inorganic membranes that may be used are, for example: SMS (Sulzer Chemtech), Silica (Pervatech), NaA (Mitsui or Smart Chemical).

The inventive dewatering is effected preferably at a temperature in the range from 20 to 200° C. at the inorganic membranes and preferably in the temperature range from 20 to 150° C. at the polymer membranes. Preference is given to carrying out the dewatering at the membranes at a temperature of from 20 to 150° C., more preferably at a temperature of from 40 to 140° C. and most preferably at a temperature of from 60 to 130° C. The removal at the membranes can be effected at any membrane, in any module or in any membrane unit, at different or identical temperature. Especially when relatively water-rich ethanol streams are to be worked up by the process according to the invention, one of which is a fresh alcohol stream and the other is a recycle stream, it may be advantageous to conduct the recycle stream to the membrane with a different temperature to the fresh alcohol, in order, for example, not to lose thermal energy inherent to the recycle stream.

In the dewatering, the pressure on the retentate side of the membrane is preferably from 0.05 to 3 MPa, preferably from 0.1 to 2 MPa. The pressure on the permeate side of the membrane is preferably from 0.0001 to 0.1 MPa, preferably from 0.001 to 0.01 MPa.

In the case of polymer membranes, the pressure difference is preferably from 0.001 to 2 MPa and, in the case of inorganic membranes, preferably from 0.001 to 3 MPa. The inventive dewatering at the membranes is preferably carried out at a pressure difference of from 0.001 to 2 MPa and more preferably from 0.1 to 0.8 MPa. The pressure difference may be the same or different at all membranes, membrane modules or membrane units used.

The pressure or the pressure difference can be generated in different ways. The pressure difference can be generated, for example, by generating an elevated pressure on the feed stream side. However, the pressure difference can, for example, also be generated by generating a reduced pressure, in particular additionally a reduced pressure (vacuum), on the permeate side of the membrane. Preferably, the pressure difference is generated by additionally generating a reduced pressure on the permeate side, since compaction of the membranes can be prevented in this way. To generate a reduced pressure, any membrane or membrane unit in the process according to the invention may be equipped with a dedicated reduced-pressure system. In order to minimize the capital investment and to save operating costs, it is, though, preferred to attach all membranes or membrane units used at the permeate side to a common reduced-pressure system.

The specific mass flow rate through the membrane (kg of permeate per square meter of membrane surface per hour) is dependent upon the water concentration of the retentate. The extrapolated pure water flow rate is employed as the mass flow rate based on the concentration. It is preferably from 1 to 100 kg/(m²·h), preferably from 5 to 30 kg/(m² ·h). The preferred pure water flow rate may be established by selection of a suitable membrane and selection of an appropriate pressure difference. The selection can be done by means of simple preliminary experiments.

It is self-evident that all membrane modules can be operated at identical or different operating parameters, under the prerequisite that they are within the abovementioned ranges.

When the separation principle of vapor permeation or pervaporation is used at the membranes in the process according to the invention, a vaporous permeate is obtained. Depending on the further intended use, it may be advantageous to condense the permeate by condensation in a heat transferrer.

The water-rich permeates obtained in the membrane units in the dewatering in the process according to the invention may be worked up separately or together. Preference is given to working up the water-rich permeates obtained together. The workup can be effected, for example, by separation at membranes, by distillation or by distillation using an azeotroping agent. A combined workup of the permeates is preferred, especially when the permeates have a water content that is greater than the concentration of the ethanol/water azeotrope, because a simple concentration of the permeate or of the combined permeate streams by means of distillation is possible in such a case. In a preferred embodiment, the permeates, together or separately, are separated by distillation into water and a distillate consisting of the ethanol/water azeotrope or consisting of the ethanol/water azeotrope and additional water, and the distillate is recycled into one of the membrane units of the process as a water-rich ethanol stream.

When the process according to the invention is a part-process in a process for preparing ETBE, it may be advantageous in particular when the permeates, together or separately, are worked up by distillation together with an ethanolic aqueous extract from an ETBE plant and then the ethanol-rich distillate is recycled into one of the membrane units of the process according to the invention as a water-rich ethanol stream.

The retentates obtained from the membrane units may be used either separately or together, or sent separately or together to a workup. Such a workup may, for example, comprise a further dewatering in a membrane unit or a distillative workup. It may be advantageous to combine the retentates from the membrane units present when their water concentrations differ by less than 1% by mass, preferably by less than 0.5% by mass, more preferably by less than 0.2% by mass and most preferably from 0 to 0.2% by mass, in particular from 0.001 to 0.1% by mass. Only when the difference in the water concentration of the two streams to be combined is less than 1% by mass can the advantages of separate workup no longer sufficiently balance out the higher capital costs, so that a combined workup is then preferred.

When the desired specification of the relatively low-water ethanol in the retentates has not yet been attained, it may be advantageous to combine the two or more retentate streams obtained from the membrane units and to dewater them once again in a further membrane unit. Such a preferred embodiment of the process according to the invention is shown schematically in FIG. 3. This embodiment of the process according to the invention is also preferably carried out in such a way that, before combination of the two streams, the water contents are brought to virtually the same value (see above) by separation in the individual membrane units.

In another embodiment of the process according to the invention, the retentate stream from the membrane unit for separating an ethanol stream with a relatively high water content is combined with the feed stream of a membrane unit for separating an ethanol stream with a relatively low water content. This may be advantageous in particular when at least two relatively water-rich ethanol streams are used that have a relatively great difference with regard to the water concentration, for example, greater than 2.5% by mass or preferably greater than 5% by mass, and more preferably from 5 to 10% by mass, the water content of the ethanol stream having the relatively small content of water preferably having a concentration that is already relatively close to the specification concentration. In this case, as far as possible, sufficient water is removed from the ethanol stream with the relatively high water content in the membrane unit that the resulting retentate has a water content that differs from the water content of the ethanol stream with the relatively low water content by not more than 1% by mass, preferably by not more than 0.5% by mass, and the retentate stream is combined with the ethanol stream with low water content and conducted as a feed stream into the membrane unit for dewatering the ethanol stream with the relatively low water content. Such an embodiment of the process according to the invention is shown schematically in FIG. 2.

Figure 1:
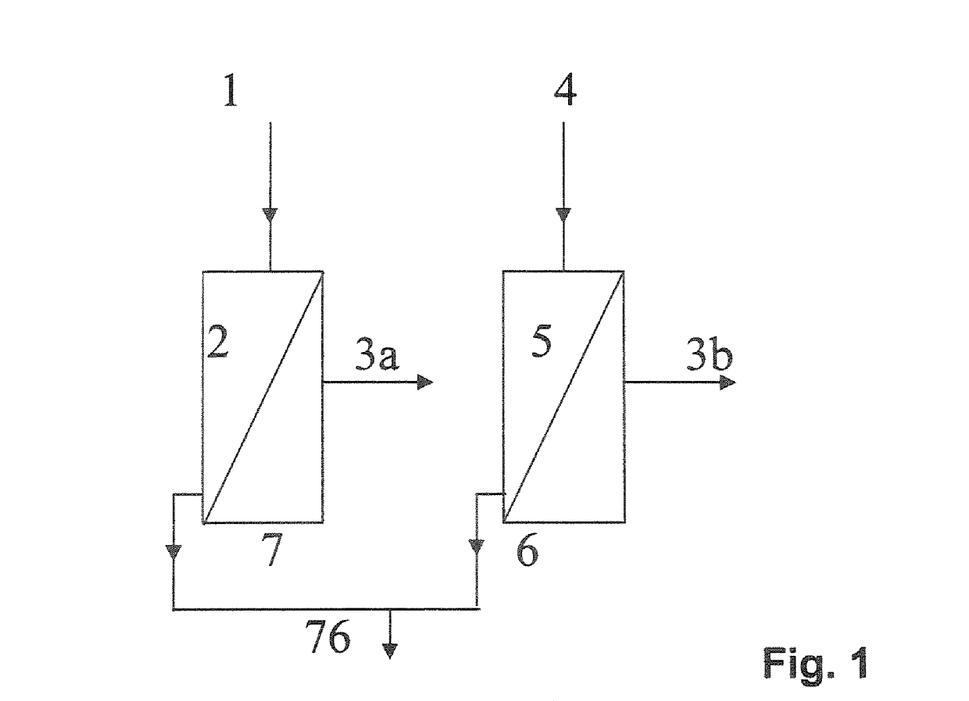
FIG. 1 is a block diagram showing one embodiment of the invention.

In the simplest case of one embodiment of the process according to the invention, the retentates are simply combined before they are sent to further use. Such an embodiment is shown in FIG. 1.

As already mentioned, the process of the present invention may be an integral part of an ETBE plant, in which case the process can be used to dewater, for example, the use alcohol and the return ethanol obtained in the ETBE process. An illustrative ETBE process into which the process of the present invention can be integrated is described below.

In a particular embodiment of the process according to the invention, the low-water ethanol prepared in accordance with the invention can be used as a reactant in an ETBE synthesis and the excess ethanol from the process of ETBE synthesis can be removed by extraction with water from the ETBE process, and this extraction stream can be fed, directly or after a distillative workup, as a relatively water-rich ethanol stream to a membrane unit. The second relatively water-rich ethanol stream used may in particular be the use alcohol that, in a commercially customary manner, has a water content in the region of the azeotropic concentration.

The use alcohol that can be used as an aqueous ethanol stream in the process according to the invention may preferably be an ethanol/water azeotropic mixture having a water content of 4.4% by mass or a mixture that has a lower water content. The water content in the use alcohol may preferably be in the range from 4.4 to 0.5% by mass, in particular in the range from 1 to 0.6% by mass. In addition, the fresh ethanol may contain higher alcohols (fusel oils) up to 1% by mass.

The return ethanol that may be used as an aqueous ethanol stream in the process according to the invention can be obtained, for example, by, in an ETBE process, extracting ethanol with water or an aqueous solution from an ethanol-containing $C_4$ hydrocarbon mixture. The ethanol can be removed from the aqueous extract by distillation. At best, the ethanol/water mixture obtained as return ethanol corresponds to the azeotrope with a water content of at least 4.4% by mass. Usually, the water content is, though, higher. Typically, the water content of the return ethanol is from 4.4 to 12% by mass, in particular from 6 to 10% by mass.

In a preferred embodiment of the process according to the invention, the return ethanol that is removed from an ethanolic hydrocarbon mixture by extraction with water or an aqueous solution and the ethanol/water azeotrope or a mixture of ethanol/water azeotrope and additional water is obtained from the extract by distillation can be worked up together with one or more of the permeates that are obtained in the membrane units and frequently have water contents greater than 40% by mass. As described above, the workup can be effected by separation at membranes, by distillation or by distillation using an azeotroping agent. Optionally, one or more permeates may be worked up together with the undistilled ethanolic water extract from an ETBE plant.

The process according to the invention can be used to obtain a stream of relatively low-water ethanol, in particular a composition containing ethanol and small amounts of water, that preferably has a water content of less than 3% by mass, preferentially less than 1% by mass, more preferably less than 0.5% by mass and most preferably less than 0.3% by mass. The composition prepared by the process according to the invention preferably has ethanol with a water content of less than 1% by mass, more preferably less than 0.3% by mass. Compositions of low-water ethanol prepared in accordance with the invention, in particular compositions that have a water content of less than 1% by mass, more preferably less than 0.3% by mass, may be used in particular as a reactant for preparing ETBE. In particular, such compositions or such ethanol are used in processes in which the reaction is catalyzed by acidic ion exchange resins. The ETBE preparation can be effected in one or more reaction stages. Processes for preparing ETBE can be taken, for example, from EP 0 071 032, U.S. Pat. No. 6,472,568, RU 2 168 490, RU 2 167 143, U.S. Pat. No. 6,107,526 or U.S. Pat. No. 5,990,361, which are incorporated by reference herein. A two-stage ETBE process in which the ethanol dewatered in accordance with the invention can preferably be used is described below.

The preferred process for preparing ETBE from technical mixtures of $C_4$ hydrocarbons I that comprise at least 1-butene, isobutene, n-butane and 2-butenes has the process steps of a) reacting portions of the isobutene present in the technical mixture with ethanol to give ETBE in the presence of an acidic catalyst, b) removing the unconverted $C_4$ hydrocarbons III from the effluent of stage a) by thermal separation processes to obtain a fraction II comprising (substantially) ETBE, c) distillatively separating the $C_4$ hydrocarbons III into a fraction IV containing at least 1-butene and isobutene, and a virtually isobutene-free fraction V containing at least 2-butenes and n-butane, d) reacting the isobutene present in fraction IV with ethanol VI in the presence of acidic catalysts to give ETBE and e) removing the unconverted $C_4$ hydrocarbons VIII from the effluent of stage d) to obtain a fraction VII comprising ETBE.

Process step a)

Process step a) is preferably carried out in such a way that the conversion of isobutene in process step a) is greater than 50%, preferably greater than 70%, preferentially greater than 80%, more preferably greater than 90% and most preferably greater than 95%. The magnitude of the conversion of isobutene can be controlled, for example, by the number of reactors used in step a) or by selection of suitable reaction conditions that the person skilled in the art can determine easily by simple preliminary experiments.

The etherification of the isobutene is carried out as an acid-catalyzed reaction. The ethanol used may be highly pure ethanol, pure ethanol or ethanol that has small amounts of impurities. The purity of the ethanol used, reported in % by mass of ethanol, is preferably greater than 90%, more preferably greater than 95%, and most preferably equal to or greater than 99%. Ethanol that has a purity of greater than or equal to 99% by mass may, for example, be bioethanol. The content of water is preferably below 3% by mass, more preferably below 1% by mass, most preferably below 0.5% by mass. The ethanol used is more preferably denatured ethanol. The ethanol used is most preferably ethanol that has ETBE as a denaturing agent, preferably in a concentration of from 0 to 5% by mass, preferably from 0.005 to 1% by mass, more preferably from 0.05 to 1% by mass, and most preferably from 0.01 to 0.2% by mass. In Germany, particular preference is given to using ethanol that has at least from 0.1 to 1% by mass of denaturing agent. Very particular preference is given to using low-water ethanol or a composition that comprises low-water ethanol and has been obtained by the process according to the invention.

For the reaction of isobutene with alcohols, especially with methanol to give methyl tert-butyl ether, various process variants have been developed (cf.: Ullmann's Encyclopedia of Industrial Chemistry, Online Version, 2004, Wiley & Sons, under Methyl tert-butyl ether, and literature cited there; Obenaus, Fritz; Droste, Wilhelm, Erdoel & Kohle, Erdgas, Petrochemie (1980), 33(6), 271 to 275; DE 26 29 769; DE 28 53 769). In principle, all of these processes are suitable for reacting the isobutene with alcohols as process step a). Preference is given to processes in which the reaction is effected in the liquid phase over an acidic ion exchange resin.

The reactors used, in which the ethanol is reacted with the isobutene up to close to the thermodynamic equilibrium, may be conventional fixed bed reactors (tube bundle reactors, adiabatic fixed bed reactors, circulation reactors, etc.). They may be operated with or without partial recycling, and the recycle stream may optionally be cooled.

In a preferred embodiment, the conversion of the isobutene is carried out in at least two stages, in which case the first stage is operated as an adiabatic fixed bed reactor with recycling (loop reactor) and the following stages as fixed bed stages without recycling and/or as a reactive distillation. The ratio of recycled amount to fresh feed ($C_4$ hydrocarbons and ethanol) is preferably from 0.5 to 20 t/t, more preferably from 1 to 5 t/t, and most preferably from 2 to 3 t/t. The reactors may be operated at temperatures of preferably from 10 to 160° C., preferentially from 30 to 110° C. The pressure in the fixed bed stages is preferably from 5 to 50 $bar_{absolute}$ (bara), preferentially from 7.5 to 20 bara, and more preferably from 8 to 13 bara. The circulation reactor preferably has an inlet temperature of from 35 to 50° C. and an outlet temperature of from 50 to 70° C. and is preferably operated at from 10 to 13 bara. Because the thermodynamic equilibrium between ethanol/isobutene and ether at low temperature is predominantly to the side of the ether, it is preferred when using a plurality of reactors to operate the first of the reactors at higher temperature (high reaction rate) than the following reactors (exploitation of the equilibrium position). In process step a), particular preference is given to using a reactor system that has three reactors connected in series of which the first reactor is operated as a loop reactor and the two reactors downstream are operated in straight pass. It may be advantageous when a plurality, preferably two, of these reactor systems are present in process step a), so that, in the event of repair work, for example, catalyst change in one reactor of one of the reactor systems, process step a) can be carried out further in the other reactor system without interruption of the process (albeit with halving of the throughput). In the case of use of reactor systems composed of three reactors, the reactors are operated preferably at a temperature of from 30 to 80° C., preferably from 40 to 75° C., and a pressure of from 5 to 20 bara, preferably from 7 to 15 bara, the temperature in the reactors preferably falling from the first to the last reactor. The reactors downstream of the circulation reactor preferably have an inlet temperature of from 30 to 50° C. and an outlet temperature of from 35 to 45° C., and are preferably likewise operated at from 8 to 13 bara.

The molar ratio of ethanol to isobutene in process step a) is preferably from 5:1 to 0.9:1, preferably from 2:1 to 1:1, and more preferably from 1.2:1 to 1:1. Because a relatively low conversion of isobutene can be accepted in process step a), a lower ethanol excess may be advantageous in comparison to process step d).

In a preferred embodiment, the addition of the ethanol to the isobutene is carried out in the presence of an acidic catalyst in such a way that at least one reaction stage is carried out as a reactive distillation. More preferably, the acid-catalyzed etherification in step a) is carried out in at least two reaction stages, in which case preferably at least one, more preferably the last reaction stage is carried out as the reactive distillation. In the fixed bed reactor(s), a reaction mixture that is close to the thermodynamic equilibrium with regard to its isobutene, ethanol and ETBE concentration is first prepared over an acidic catalyst from the isobutenic technical hydrocarbon mixture I and ethanol. The conversion of the isobutene is preferably more than 90%. This mixture is fed into the reactive distillation column in the next/last reaction stage, where a further portion of the isobutene is converted to the ether. More preferably, process step a) is performed in a reactor system that has three reactors connected in series, preferably fixed bed reactors, of which the first is preferably operated in loop mode and the two downstream reactors in straight pass, and has a reactive distillation, the reactor effluent of the last of the reactors connected in series being conducted into the reactive distillation.

Depending on the pressure, the isobutene is reacted with ethanol to give ETBE in the reactive distillation preferably in the temperature range from 40 to 140° C., preferably from 60 to 90° C., more preferably from 65 to 85° C. (temperature in the region of the column in which the catalyst is disposed. The bottom temperature of the column may be significantly higher). The reactive distillation column is preferably operated at pressures, measured at the top of the column, of from 3 bara to 15 bara, preferably from 7 bara to 13 bara, in particular from 8 bara to 11 bara.

When process step a) of the preferred ETBE process has a reactive distillation, the $C_4$ hydrocarbon mixture comprising isobutene is, as described in DE 101 02 082 for MTBE, fed together with ethanol into the first of the prereactors. In this case, the ethanol is preferably used in excess. In the prereactors, a mixture forms in which isobutene, ethanol and ETBE are present in equilibrium or virtually in equilibrium. This reaction mixture is introduced into the reactive distillation column.

In the feed of the reactive distillation column, more ethanol may be present than is needed for the full conversion of the isobutene still present. However, the ethanol excess should be such that a sufficient amount of ethanol is present for the azeotrope of ethanol and $C_4$ hydrocarbons that forms.

The feeding to the reactive distillation column is preferably effected below the reactive packing, preferably from 3 to 13, more preferably from 4 to 10 theoretical plates below the reactive packing.

Optionally, when the ethanol content in the column feed to the reactive distillation column is below the maximum permissible value, additional ethanol can be added. In addition, ethanol feeding can be effected via a separate device at the top of the reactive distillation column above the column feed below a liquid distributor or in a liquid distributor above or in the region of the reactive zone, preferably in the region of the reactive zone. Additional feeding of ethanol can be effected, for example, into the reflux of the column or directly into the reactive packings. The additional ethanol addition should be such that, in the packings of the reactive zone, the ethanol content in the liquid phase is preferably greater than or equal to 1.5% by mass, preferentially greater than or equal to 2% by mass and more preferably from 2 to 3% by mass. The addition of ethanol into the reaction zone ensures that, in spite of the depletion, sufficient ethanol is available as a reactant.

The reactive distillation column above the catalyst packing preferably has a region of pure distillative separation, more preferably with from 5 to 20, in particular with from 7 to 10 theoretical plates. The catalyst zone can be estimated with a distillative action of from 1 to 5 theoretical plates per meter of packing height. The separation zone below the catalyst may preferably include from 12 to 36, in particular from 20 to 30 theoretical plates. The height of the catalyst zone/reactive zone can be determined by simple preliminary experiments as a function of the desired isobutene conversion. The amount of catalyst is preferably selected at such a level that an isobutene conversion of from 30 to 98%, preferably from 50 to 95%, and more preferably from 75 to 90%, based on the isobutene content in the feed to the reactive distillation, is achieved.

The hydraulic loading in the catalytic packing of the column is preferably from 10% to 110%, preferably from 20% to 90%, and more preferably from 35 to 75%, of its flood point loading. Hydraulic loading of a distillation column is understood to mean the uniform flow demand on the column cross section by the ascending vapor stream and the refluxing liquid stream. The upper loading limit indicates the maximum loading by vapor and reflux liquid, above which the separating action falls due to entrainment or accumulation of the reflux liquid by the ascending vapor stream. The lower loading limit indicates the minimum loading, below which the separating action falls or collapses due to irregular flow or emptying of the column—for example of the trays (Vauck/Müller, "Grundoperationen chemischer Verfahrenstechnik", p. 626, VEB Deutscher Verlag für Grundstoffindustrie). At the flood point, the shear stresses transferred from the gas to the liquid are so great that the entire amount of liquid is entrained with the gas in the form of drops, or that there is phase inversion in the column (J. Mackowiak, "Fluiddynamik von Kolonnen mit modernen Füllkörpern und Packungen für Gas/Flüssigkeitssysteme", Otto Salle Verlag 1991).

The reactive distillation column is preferably operated with reflux ratios less than 1.5, in particular with those that are greater than 0.6 and less than 1.2, preferably greater than 0.7 and less than 1.1.

The generic term reactive distillation includes all process technology measures in which distillation and reaction are carried out simultaneously. In the reactors described, this simultaneous operation is achieved by particular design of the packings in a column. However, it is also possible in the preferred ETBE process to spatially separate these regions without dispensing with the advantages of a reactive distillation.

In one process variant, the reactive distillation column may be designed as a distillation column with one or more external reactors that contain the catalyst and are operated in a bypass stream, known as side reactors.

The top product of the reactive distillation column contains essentially a $C_4$ hydrocarbon mixture and ethanol.

The catalyst used both in the fixed bed stages and in any reactive distillation column present is preferably a solid substance that is soluble neither in the feedstock mixture nor in the product mixture and has acidic sites on its surface. The catalyst should not release any acidic substances to the product mixture under reaction conditions, because this release can lead to yield losses.

The activity of the catalysts is preferably selected such that they catalyze the addition of ethanol to isobutene under the reaction conditions but barely catalyze the addition to linear butenes. Moreover, the catalysts should, as far as possible, not catalyze or only slightly catalyze the oligomerization of linear butenes and dialkyl ether formation from two molecules of ethanol used. With regard to a high yield of 1-butene, the activity for the isomerization of 1-butene to 2-butene should preferably be low.

The solid catalysts used may, for example, be zeolites, acid-activated bentonites and/or aluminas, sulfonated zirconium oxides, montmorillonites or acidic ion exchange resins.

A group of acidic catalysts used, which is preferred in the ETBE process in process step a), is that of solid ion exchange resins, in particular those having sulfonic acid groups. Suitable ion exchange resins are, for example, those that are prepared by sulfonating phenol/aldehyde condensates or cooligomers of aromatic vinyl compounds. Examples of aromatic vinyl compounds for preparing the cooligomers are styrene, vinyltoluene, vinylnaphthalene, vinylethylbenzene, methylstyrene, vinylchlorobenzene, vinylxylene and divinylbenzene. In particular, the cooligomers that are formed by reaction of styrene with divinylbenzene are used as a precursor for the preparation of ion exchange resins with sulfonic acid groups. The resins may be prepared in gel form, macroporous form, or sponge form.

The properties of these resins, in particular specific surface area, porosity, stability, swelling or shrinkage, and exchange capacity can be varied by virtue of the preparation process.

In the ETBE process, the ion exchange resins may be used in their H-form. Strongly acidic resins of the styrene-divinylbenzene type are sold, inter alia, under the following trade names: Duolite C20, Duolite C26, Amberlyst 15, Amberlyst 35, Amberlite IR-120, Amberlite 200, Dowex 50, Lewatit SPC 118, Lewatit SPC 108, K2611, K2621, OC 1501.

The pore volume is preferably from 0.3 to 0.9 ml/g, in particular from 0.5 to 0.9 ml/g. The particle size of the resin is preferably from 0.3 mm to 1.5 mm, in particular from 0.5 mm to 1.0 mm. The particle size distribution can be selected relatively narrowly or widely. For example, ion exchange resins with very uniform particle size (monodisperse resins) can be used. The capacity of the ion exchanger is, based on the supply form, preferably from 0.7 to 2.0 eq/l, in particular from 1.1 to 2.0 eq/l, or preferably from 0.5 to 5.5 mol/kg, in particular from 0.8 to 5.5 mol/kg (the capacity data in mol/kg each relate to the ion exchange resin dried to constant weight in a warm nitrogen stream at, for example, 105° C.).

In the reaction part of any reactive distillation present in process step a), the same catalysts may be used as are used in the simple reactors. In the reactive distillation column, the catalyst may either be integrated in the packing, for example KataMax® (as described in EP 0 428 265), KataPak® (as described in EP 0 396 650 or DE 298 07 007.3 U1) or polymerized on shaped bodies (as described in U.S. Pat. No. 5,244,929).

Process Step b)

In step b), the unconverted $C_4$ hydrocarbons III are removed from the effluent of step a) by thermal separation processes, for example, by distillation or fractionation. When process step a) includes a reactive distillation, process step b) can take place partly or fully actually in the course of performance of the reactive distillation, and a separate step b) can in some cases be dispensed with.

Process step b) can preferably be carried out in a distillation column. The distillation column preferably has a number of theoretical plates of from 25 to 50, preferably from 30 to 40. The feed to this column is preferably in the region of the 10th to 15th theoretical plate (from the top). The distillation in process step a) is carried out preferably at a pressure of from 3 to 10 bara, preferably from 4 to 7 bara, a preferred top temperature of from 30 to 70° C., more preferably from 45 to 60° C., and a preferred bottom temperature of from 105 to 125° C., more preferably from 110 to 120° C.

The thermal separation process is preferably carried out in such a way that the bottom product obtained is a fraction comprising essentially ETBE and the top product obtained is a fraction containing essentially unconverted $C_4$ hydrocarbons and ethanol. When the butene oligomers are removed before the reaction with ethanol, the bottom product of the reactive distillation column preferably comprises ETBE.

The top product of process step b), i.e., the top product of the reactive distillation or of the thermal separation, can be fed directly to a further separation in process step c) or else first be worked up in one or more workup steps.

Process step f)

Between process steps b) and c), the preferred ETBE process preferably has a further process step f) in which the ethanol is first removed fully or virtually fully from the unconverted $C_4$ hydrocarbons in the top product of process step b), i.e., the top product from the reactive distillation or from the thermal separation that comprises essentially unconverted $C_4$ hydrocarbons and ethanol.

The top product from process step b) that is obtained at the top of the distillation column or reactive distillation column is preferably transferred into an extraction column into which water is fed as an extractant in countercurrent via a feed disposed at the top. The extractant can be withdrawn via the outlet at the bottom of the column. At the top of the column, the product obtained from the extraction is the stream composed of hydrocarbons III unconverted in stage a) and, if appropriate, b). This product can be fed into process step c).

Process step f) can preferably be carried out in an extraction column. The extraction column preferably has from 5 to 20, preferentially from 10 to 15 theoretical plates. The extraction in process step f) is preferably carried out at a pressure of from 5 to 12 bara, preferably from 7 to 10 bara. The extraction in process step f) is preferably carried out at a temperature of from 30 to 60° C. and preferentially from 35 to 45° C. The ratio of water extractant to the top product from process step b) or a) is preferably from 0.05 to 0.5, preferentially from 0.1 to 0.25 and more preferably from 0.15 to 0.2.

The ethanol-enriched extractant obtained in the bottom of the extraction column can be separated by distillation and the ethanol thus obtained can be fed as a water-rich ethanol stream to the process according to the invention in which it is worked up to give relatively low-water ethanol that is fed back to the ETBE process as a starting material in steps a) or d).

Process Step c)

After the removal of the ETBE and optionally after removal of the unconverted ethanol, the hydrocarbon stream obtained from step b) or f) is separated by distillation in step c). The distillative separation is carried out in such a way to obtain a fraction IV containing at least 1-butene and isobutene (top fraction) and a virtually isobutene-free fraction V (bottom fraction) containing at least 2-butenes and n-butane, and preferably having less than 5% by mass, preferentially less than 1% by mass, and more preferably less than 0.1% by mass of isobutene. Fraction V contains at least 95% by mass, preferably at least 99% by mass, more preferably at least 99.8% by mass of the 2-butenes originally present in the hydrocarbon stream obtained as the product of step c). Fraction IV has preferably less than 1% by mass, more preferably less than 0.2% by mass of n-butane. The distillative separation can be carried out in apparatus used customarily for the separation of such hydrocarbon mixtures. Such apparatus may, for example, be distillation or fractionation columns.

Preference is given to carrying out the separation in a superfractionation column. The feed to this column is preferably in the lower half, preferably in the lower third of the column. Owing to the narrow boiling point of the mixture to be separated, the distillation is preferably carried out in a column having preferably more than 100, preferentially more than 125, more preferably having 150 or more theoretical plates, and most preferably having 150 to 200 theoretical plates. The reflux ratio (reflux amount to distillate withdrawal) is, depending on the number of stages realized and on the operating pressure, preferably less than or equal to 20, preferentially less than or equal to 14, more preferably less than or equal to 11, and most preferably from 8 to 11. The condensation can be carried out against cooling water or air. The distillate vessel is preferably designed as a liquid-liquid separator. As a result, any water present in the feed stream can be removed as a second phase in the distillate vessel and a technical water-free bottom product can be obtained.

The separation in process step c) is preferably carried out at a pressure of from 4 to 10 bara, preferentially at a pressure of from 5 to 7 bara. The temperature at which the separation is carried out is preferably from 35 to 65° C., preferentially from 40 to 50° C.

To heat the evaporator of the column, it is possible to use a customary heat transferrer, for example steam or warm water, and also preferably waste heat from other processes. In the latter case, it may be advantageous to equip the column with more than one evaporator. The column is preferably equipped as a simple column with at least one evaporator and at least one condenser. Owing to the high energy demand and the small temperature difference between bottom and top of the column, energy-saving connections are particularly preferred embodiments. Reference is made here by way of example to the method of vapor compression. A further particularly preferred connection is two-pressure connection (double effect distillation) in integration with a second column. The second column may preferably be a parallel-connected column with the same or different separation task. In this case, one of the columns is operated at such high pressure that its condensation temperature is sufficient to heat the other column. In the connection of columns with different separation tasks for heating purposes, it is possible in principle to connect any suitable column from the ETBE process, but also a column that is present at the plant site outside the ETBE process, with the column of process step c).

Process Step d)

In the preferred ETBE process, the isobutenic fraction IV obtained from step c) is converted in a further reaction step (step d) in which the remaining isobutene is converted by addition of ethanol to give ETBE.

Just as the etherification in step a), the etherification of the isobutene is carried out as an acid-catalyzed reaction. The ethanol used may be highly pure ethanol, pure ethanol or ethanol that has small amounts of impurities. The purity of the ethanol used, reported in % by mass of ethanol, is preferably greater than 90%, more preferably greater than 95% and most preferably equal to or greater than 99%. Ethanol having a purity of greater than or equal to 99% by mass is supplied in Europe, for example, as bioethanol. The content of water is preferably below 3% by mass, more preferably below 1% by mass, most preferably below 0.5% by mass. In the process, it may be advantageous to use denatured ethanol. The ethanol used is more preferably ethanol that has ETBE as a denaturing agent, preferably in a concentration of from 0 to 5% by mass, preferentially from 0.005 to 1% by mass, more preferably from 0.05 to 1% by mass, and most preferably from 0.01 to 0.2% by mass. In Germany, preference is given to using ethanol that has from 0.1 to 1% by mass of denaturing agent. The use of ethanol denatured with ETBE prevents extraneous substances from being introduced into the process. Again, preference is given here too to using low-water ethanol or a composition comprising low-water ethanol that has been obtained by the process according to the invention.

For the reaction of isobutene with alcohols, in particular with methanol to give methyl tert-butyl ether, various process variants have been developed (cf.: Ullmann's Encyclopedia of Industrial Chemistry, Online Version, 2004, Wiley & Sons, under Methyl tert-butyl ether, and literature cited there; Obenaus, Fritz; Droste, Wilhelm, Erdoel & Kohle, Erdgas, Petrochemie (1980), 33(6), 271 to 275; DE 26 29 769; DE 28 53 769). In principle, all known processes for reacting the isobutene with alcohols are suitable for use as process step d).

Preference is given to using processes in which the reaction is effected in the liquid phase over an acidic ion exchange resin. The reactors used, in which the ethanol is reacted with the isobutene up to close to the thermodynamic equilibrium, may be conventional fixed bed reactors (tube bundle reactors, adiabatic fixed bed reactors, circulation reactors). They may be operated with or without partial recycling, and the recycle stream may optionally be cooled. In step d), particular preference is given to using a reactor system that has two reactors, in particular fixed bed reactors. Preference is given to operating the two reactors in straight pass.

The reactors may be operated at temperatures of from 25 to 110° C., preferably at temperatures of from 30 to 70° C., and more preferably at temperatures of from 35 to 50° C. The pressure is preferably from 5 to 50 bara, preferably from 10 to 20 bara, and more preferably from 10 to 13 bara. Because the thermodynamic equilibrium between ethanol/isobutene and ether at low temperature is predominantly on the side of the ether, it is preferred in the case of use of a plurality of reactors to operate the first of the reactors at higher temperature (high reaction rate) than the following reactors (exploitation of the equilibrium position).

The molar ratio of ethanol to isobutene in the feed to process step d) is preferably in the range from 25:1 to 1:1, more preferably from 15:1 to 3:1, and more preferably in the range from 10:1 to 5:1.

The catalysts used may preferably be those as described for process step a), the preferred ETBE process being performable such that in each case the same catalyst or different catalysts may be used in step a) and d). Preference is given to using the same catalysts in steps a) and d).

In a preferred embodiment, the addition of the ethanol to the isobutene is carried out in the presence of an acidic catalyst, in such a way that at least one reaction stage is carried out as a reactive distillation. More preferably, the acid-catalyzed etherification in step d) is carried out in at least two reaction stages, in which case preferably at least one, more preferably the last reaction stage is carried out as the reactive distillation. In the fixed bed reactor(s), a reaction mixture that is close to the thermodynamic equilibrium with regard to its isobutene, ethanol and tert-butyl ether concentration is first prepared over an acidic catalyst from the isobutenic fraction IV and the ethanol VI. In this reaction step, the residual content of isobutene is preferably converted to such an extent that the required purity of the 1-butene can be achieved with the downstream reactive distillation. This mixture is fed into the next/last reaction stage in the reactive distillation column, where a further portion of the isobutene is converted to the ether. Most preferably, step d) is carried out in a reactor system that has two reactors connected in series and a reactive distillation column, the two reactors preferably being operated in straight pass, and the effluent from the second reactor is fed into the reactive distillation column.

In the reaction part of the reactive distillation column, the same catalysts as described above for the simple embodiment of the process stage without the use of a reactive distillation may be used.

In the reactive distillation column, the catalyst may either be integrated in the packing, for example KataMax® (as described in EP 0 428 265), KataPak® (as described in EP 0 396 650 or DE 298 07 007.3 U1) or polymerized onto shaped bodies (as described in U.S. Pat. No. 5,244,929).

The reaction of the isobutene with ethanol to give ETBE is effected in the reactive distillation in the temperature range from 10 to 140° C., preferably from 30 to 70° C., more preferably from 35 to 50° C. (temperature in the region of the column in which the catalyst is disposed. The bottom temperature of the column may be significantly higher).

In particular, the ETBE is prepared by reaction with ethanol in a manner as described in DE 101 02 082 for the reaction of methanol with isobutene to give MTBE. The $C_4$ hydrocarbon mixture comprising isobutene is fed into the prereactor(s) together with ethanol. The ethanol is preferably used in excess. In the prereactors, a mixture forms in which isobutene, ethanol and ETBE are in equilibrium or virtually in equilibrium. This reaction mixture is introduced into the reactive distillation column.

The feed to the reactive distillation column may comprise more ethanol than is needed for the full conversion of the isobutene still present. However, the alcohol excess should be such that a sufficient amount of ethanol is present for the azeotrope of ethanol and $C_4$ hydrocarbons that forms.

Optionally, for example when the ethanol content in the column feed is below the maximum permissible value, additional ethanol may be added to the column feed. In addition, ethanol feeding may be effected via a separate device at the top of the reactive distillation column above the column feed below a liquid distributor or in a liquid distributor above or in the region of the reactive zone, preferably in the region of the reactive zone. Additional feeding of ethanol can be effected, for example, into the reflux of the column or directly into the reactive packings. The additional ethanol addition should be such that the ethanol content in the liquid phase in the packings of the reactive zone is preferably greater than or equal to 1.5% by mass, preferably greater than or equal to 2% by mass, and more preferably from 2 to 3% by mass.

Preferably, the reactive distillation column has a region of pure distillative separation above the catalyst packing, more preferably having from 5 to 20, in particular having from 7 to 10 theoretical plates. The catalyst zone can be estimated at a distillative action of from 1 to 5 theoretical plates per meter of packing height. The separation zone below the catalyst may preferably include from 12 to 36, in particular from 20 to 30 theoretical plates. The height of the catalyst zone/reactive zone can be determined by simple preliminary experiments depending upon the desired isobutene conversion. The amount of catalyst is preferably selected at such a level that a residual isobutene content in the top product of less than 2000 ppm by mass (ppmw), preferably less than 1500 ppmw is achieved.

The feed to the reactive distillation column may be above or below the catalyst zone. The feed to the reactive distillation column is preferably below the reactive packing, preferably from 3 to 13, more preferably from 4 to 10 theoretical plates below the reactive packing.

The reactive distillation column is operated at pressures, measured at the top of the column, of from 3 bara to 10 bara, preferably from 4 bara to 7 bara, in particular from 5 bara to 6 bara. The hydraulic loading in the catalytic packing of the column is preferably from 10% to 110%, preferentially from 20% to 90% and more preferably from 35 to 75% of its flood point loading. Hydraulic loading of a distillation column is understood to mean the uniform flow demand on the column cross section by the ascending vapor stream and the refluxing liquid stream. The upper loading limit indicates the maximum loading by vapor and reflux liquid, above which the separating action falls due to entrainment or accumulation of the reflux liquid by the ascending vapor stream. The lower loading limit indicates the minimum loading, below which the separating action falls or collapses owing to irregular flow or emptying of the column—for example of the trays (Vauck/Müller, "Grundoperationen chemischer Verfahrenstechnik", p. 626, VEB Deutscher Verlag für Grundstoffindustrie.).

At the flood point, the shear stresses transferred by the gas to the liquid become so great that the entire amount of liquid is entrained in the form of drops with the gas or that there is phase inversion in the column (J. Mackowiak, "Fluiddynamik von Kolonnen mit modernen Füllkörpem und Packungen für Gas/Flüssigkeitssysteme", Otto Salle Verlag 1991).

The reactive distillation column is preferably operated with reflux ratios of from 0.2 to 4, in particular with those which are from 0.4 to 2, preferably from 0.5 to 1.

When a reactive distillation column is used as the last step in stage d), step d) and also step e), namely the removal of the ETBE from the unconverted hydrocarbons, can take place at least partly therein. It is then possible in some cases to dispense with a further step e).

The generic term reactive distillation includes all process technology measures in which distillation and reaction are carried out simultaneously. In the reactors described, this simultaneous operation is achieved by a particular design of the packings in a column. In the preferred ETBE process, it is, though, also possible to spatially separate these regions without dispensing with the advantages of a reactive distillation.

In one process variant, the reactive distillation column is designed as a distillation column with one or more external reactor(s) that contain(s) the catalyst and is/are operated in a bypass stream.

Process Step e)

When no reactive distillation column is used for etherification and simultaneous separation in process step d), a dedicated step e) has to be provided in the preferred ETBE process, in which the product from process step d) is separated into the ETBE-containing bottom stream and a stream that comprises the unconverted hydrocarbons. Otherwise, the distillative separation is effected as per process step e) in the reactive distillation column. The separation can be effected, for example, by feeding the effluent from the reactor of process step d) into a distillation column. The column can be equipped with a bottom evaporator and a condenser for the top product. The bottom product obtained from the distillation column is ETBE and in some cases excess ethanol. The top product can be returned partly as reflux into the column. The other portion can be fed to process step h).

The column has preferably more than 20, preferentially more than 25, more preferably from 30 to 50 theoretical plates. The reflux ratio is, depending on the number of stages realized, preferably less than or equal to 1. More preferably, the reflux ratio is set to a value of from 0.9 to 0.6. The condensation can be carried out against cooling water or air. To heat the evaporator of the column, steam, for example, can be used. It may be advantageous to pass the feed stream to the column in at least partly pre-evaporated form or to flash it directly into the column. For this purpose, heat is preferably supplied to the feed stream in an external heat transferrer, for example, by utilizing waste heat. To achieve partial evaporation, a kettle evaporator is the preferred embodiment of the heat transferrer. It may also be advantageous when an intermediate evaporator heated to a low temperature level with process heat or waste heat is used in the lower section of the column.

In process step e), the feed to the column is preferably at the 10th to 15th theoretical plate. The column is preferably operated with a pressure of from 4 to 11 bara, preferably from 5 to 8 bara. The top temperature of the column used in process step e) is preferably from 40 to 70° C., preferentially from 45 to 60° C.

When the top product of process step e), irrespective of whether the step has been carried out in a distillation column or reactive distillation column, still has residual amounts of ethanol in the $C_4$ hydrocarbons, it may be advantageous to scrub them out with water in at least one additional extraction step. This scrubbing may be carried out by known standard industrial processes, for example in an extraction column or in a cascade of mixers and separating vessels (see process step h)).

The bottom product that contains ETBE and possibly excess ethanol may be used directly or sent to a workup, for example, a further distillation, in which the ETBE is removed from the remaining constituents.

In a further preferred embodiment of the process, the bottom product obtained in the reactive distillation or distillation of steps d) or e), that comprises ETBE and any unconverted ethanol, is returned fully or partly into step a) and/or b). This embodiment is advantageous especially when the reaction in step d) is operated with a stoichiometric excess of ethanol. In this variant, the reaction in step d) is preferably carried out only in fixed bed reactors and a distillative separation in step e) is preferably carried out in a distillation column. The unconverted $C_4$ hydrocarbons VIII are obtained as the top product, and the bottom product that is obtained and contains at least ETBE and in some cases unconverted ethanol is returned fully or partly into step a) and/or b). When process step d) is carried out with a large ethanol excess, for example, with a molar ratio of ethanol to isobutene of greater than 2:1, in particular greater than 5:1, the bottom product obtained in step e) is a mixture that contains substantially ethanol and can therefore be returned particularly efficiently as a feedstock into stage a). In this embodiment, the ETBE is obtained exclusively as a bottom product of process step b). For distillative workup of the bottom product from process step e), process step b) is utilized in this embodiment.

Process Step h)

It may be advantageous when the top product from process step d) or e) that is obtained at the top of the distillation column or reactive distillation column is transferred into an extraction column into which water is fed as the extractant in countercurrent via a feed disposed at the top. The extractant can be withdrawn via the outlet at the bottom of the column. At the top of the column, the product obtained from the extraction is the stream of hydrocarbons VIII unconverted in stage d) and, if appropriate, e). This can be sent to a further use, for example a workup to 1-butene (process step i)).

Process step h) can preferably be carried out in an extraction column. The extraction column has preferably from 5 to 20, preferentially from 10 to 15, theoretical plates. The extraction in process step h) is carried out preferably at a pressure of from 5 to 12 bara, preferentially from 7 to 10 bara. The extraction in process step h) is preferably carried out at a temperature of from 30 to 60° C., more preferably from 35 to 45° C. The ratio of extractant, especially water, to the top product from process step d) or e) is preferably from 0.05 to 0.5, preferentially from 0.1 to 0.25, and more preferably from 0.15 to 0.2.

The extractant that has been enriched with ethanol and is obtained in the bottom of the extraction column can be separated by distillation and the ethanol thus obtained can be fed as a water-rich ethanol stream to the process according to the invention in which it is dried to give relatively low-water ethanol which is fed back to the ETBE process as a starting material in steps a) or d).

Process Step i)

1-Butene can be removed by distillation as a further product of value from the $C_4$ hydrocarbon mixture VIII of unconverted hydrocarbons that has been obtained from the reactive distillation or distillation in step e), may have been freed of ethanol and comprises essentially 1-butene, isobutane and low boilers. The 1-butene is removed preferably by distillation of the mixture VIII in one or more distillation columns.

In a preferred embodiment, the 1-butene is removed in a distillation column in which the bottom product obtained is very pure 1-butene. The top product obtained is an isobutane-rich fraction that may additionally comprise low boilers (for example $C_3$ hydrocarbons).

The separation is preferably carried out in a superfractionation column. The feed to this column is preferably into the upper half, preferentially into the lower half of the upper half of the column. Due to the narrow boiling point of the mixture to be separated, the column is designed with preferably more than 100, preferentially more than 125, more preferably with 150 or more, and most preferably with from 150 to 200, theoretical plates. The reflux ratio (reflux amount to distillate withdrawal) is, depending on the number of stages realized and on the operating pressure, preferably less than or equal to 100, preferentially less than 70, more preferably from 30 to 60. The condensation may be carried out against cooling water or air. The distillate vessel is preferably designed as a liquid-liquid separator. As a result, any water present in the feed stream can be removed as the second phase in the distillate vessel and a technically water-free bottom product can be obtained.

The separation in process step i) is preferably carried out at a pressure of from 5 to 11 bara, preferably at a pressure of from 6 to 8 bara. The top temperature at which the separation is carried out is preferably from 35 to 65° C., preferentially from 45 to 50° C. When thermal integration is intended, it may be advantageous to carry out process step i) at higher temperature and hence higher pressure.

To heat the evaporator of the column, a customary heat transferrer, for example, steam or warm water and preferably waste heat from other processes may be used. In the latter case, it may be advantageous to equip the column with more than one evaporator. The column is preferably equipped as a simple column with at least one evaporator and at least one condenser. Due to the high energy requirements and the small temperature difference between bottom and top of the column, energy-saving connections are particularly preferred embodiments. Reference is made here by way of example to the method of vapor compression. A further particularly preferred connection is two-pressure connection (double effect distillation) in integration with a second column. The second column may preferably be a parallel-connected column with the same or different separation tasks. In this case, one of the columns is operated at such high pressure that its condensation temperature is sufficient to heat the other column. In the connection of columns with different separation tasks for heating purposes, it is possible in principle to connect any suitable column from the ETBE process, but also a column which is present at the plant location outside the ETBE process, with the column of process step i). More preferably, the second column is the $C_4$ separation column from process step c). In this case, one of the columns is operated at such high pressure that its condensation temperature is sufficient to heat the other column.

In a further preferred embodiment, low boilers are removed as the top product in a first distillation column; in the bottom of the column, a mixture containing mainly 1-butene and isobutane is obtained. In a second column, this bottoms mixture is separated into 1-butene that is obtained as the bottom product and an isobutane-rich fraction (top product).

Pure 1-butene prepared by the preferred ETBE process contains preferably less than 5000 ppmw (ppm by mass), preferably less than 2000 ppmw and more preferably less than 1500 ppmw of isobutene, and is a sought-after intermediate. It is used, for example, as a comonomer in the preparation of polyethylene (LLDPE or HDPE) and of ethylene-propylene copolymers. It also finds use as an alkylating agent and is the starting material for the preparation of butan-2-ol, butene oxide, and valeraldehyde. A further use of the virtually isobutene-free 1-butene prepared is the preparation of n-butene oligomers, in particular by the octol process.

In process step i), an isobutane-rich fraction is typically obtained in addition to the 1-butene (depending on the starting composition of the $C_4$ hydrocarbons). This can be purified further, preferably to pure isobutane. Purification to give pure isobutane can be effected, for example, by full hydrogenation of the alkenes still present to alkanes and subsequent distillation. The isobutane obtained in the workup has preferably a purity of at least 90% by mass of isobutane, more preferably 95% by mass of isobutane, and contains preferably less than 1000 ppmw, more preferably less than 200 ppmw, of olefins.

ETBE Process Feedstocks

In the preferred ETBE process, all technical $C_4$ hydrocarbon mixtures typically available may be used. Suitable isobutenic $C_4$ streams are, for example, $C_4$ fractions from crackers (for example steamcrackers, hydrocrackers, catcrackers), mixtures from Fischer-Tropsch syntheses, mixtures from the dehydrogenation of butanes, mixtures from skeletal isomerization of linear butenes and mixtures formed by metathesis of olefins. These techniques are described in the technical literature (K. Weissermel, H. J. Arpe, Industrielle Organische Chemie, Wiley-VCH, 5th edition, 1998, page 23-24; 65-99; 122-124).

Preference is given to using $C_4$ fractions from steamcrackers that are operated primarily for the production of ethene and propene and in which the raw materials used are, for example, refinery gases, naphtha, gas oil, LPG (liquefied petroleum gas) and NGL (natural gas liquid), or catcrackers. The $C_4$ cuts obtained as a by-product contain, depending on the cracking process, different amounts of isobutene. Further main constituents are 1,3-butadiene, 1-butene, c-2-butene, t-2-butene, n-butane and i-butane. Typical isobutene contents in the $C_4$ fraction are from 18 to 35% by mass, in the case of $C_4$ fractions from steamcrackers, from 10 to 20% by mass in the case of fluid catcrackers (FCC).

For the ETBE process, it may be advantageous to remove polyunsaturated hydrocarbons such as 1,3-butadiene from the use mixture. This removal can be done by known processes, for example, by extraction, extractive distillation or complex formation (cf. K. Weissermel, H. J. Arpe, Industrielle Organische Chemie, Wiley-VCH, 5th edition, 1998, pages 119 to 121).

One alternative to the removal of the polyunsaturated hydrocarbons is a selective chemical conversion. For example, 1,3-butadiene can be hydrogenated selectively to linear butenes, as described, for example, in EP 0 523 482. It is also possible to remove the 1,3-butadiene at least partly by selective conversions of the 1,3-butadiene, for example, dimerization to cyclooctadiene, trimerization to cyclododecatriene, polymerization or telomerization reactions. When a crack-$C_4$ cut was used as the raw material, a hydrocarbon mixture (raffinate I or hydrogenated crack-$C_4$ ($HCC_4$)) always remains and contains mainly the saturated hydrocarbons, n-butane and isobutane and the olefins isobutene, 1-butene and 2-butenes.

In the ETBE process, in an additional purification stage that is connected upstream of one or more of process steps a), b), c), d), e) or f), polyunsaturated hydrocarbons present in the $C_4$ hydrocarbon streams are preferably catalytically and selectively hydrogenated. More preferably, such a purification stage is provided at least before process step a) or c) and most preferably before process stage c), especially when it cannot be ruled out that the technical $C_4$ hydrocarbon streams used comprise polyunsaturated hydrocarbons.

The polyunsaturated hydrocarbons are mainly 1,3-butadiene; 1,2-butadiene, butenine and 1-butine are present, if at all, in a significantly smaller amount. The hydrogenation can be effected in a one-stage or multistage hydrogenation process in the liquid phase over a palladium catalyst. To lower the content of 1,3-butadiene below preferably 1000 ppmw, a moderator that increases the selectivity of the palladium catalyst is added in the last stage of the hydrogenation. The moderator used is preferably carbon monoxide which is added in a fraction of from 0.05 to 100 ppm by mass (ppmw). The content of polyunsaturated hydrocarbons in the feed to this stage should be below 1%, preferably below 0.5%. In the literature, this type of selective hydrogenation of residual contents of 1,3-butadiene is known under the name SHP (selective hydrogenation process) (cf. EP 0 081 041; Erdöl, Kohle, Erdgas, Petrochem. 1986, 39, 73).

When amounts of more than 1% of polyunsaturated hydrocarbons such as 1,3-butadiene are present in the isobutenic $C_4$ streams, they are preferably converted in upstream hydrogenations. These hydrogenations are preferably carried out in the liquid phase over a palladium catalyst. Depending on the content of unsaturated hydrocarbons, the hydrogenation may be carried out in a plurality of stages. For the conversion of crack-$C_4$ from a steamcracker with a content of 1,3-butadiene of typically from 38 to 45%, a two-stage version of the hydrogenation has been found to be useful. In this case, individual or all stages may be equipped with partial product recycling. In the effluent, concentrations of 1,3-butadiene of less than 1% are thus obtainable, so that a further conversion can be effected in a selective hydrogenation (SHP).

The hydrocarbon mixtures with isobutene and linear butenes used in the ETBE process preferably have the following compositions, a hydrogenation or selective hydrogenation being carried out before one of steps a) to d), preferably before step a) or c), depending on the content of unsaturated hydrocarbons.

TABLE 1

Typical compositions of technical hydrocarbon mixtures which can be used in the ETBE process.

| Component | Steamcracker | | Steameracker | | Catcracker | |
| --- | --- | --- | --- | --- | --- | --- |
| | $HCC_4$ | $HCC_4$/SHP | Raff. I | Raff. I/SHP | $CC_4$ | $CC_4$/SHP |
| Isobutane [% by mass] | 1–4.5 | 1–4.5 | 1.5–8 | 1.5–8 | 36–37 | 36–37 |
| n-Butane [% by mass] | 5–8 | 5–8 | 6–15 | 6–15 | 12–14 | 12–14 |
| trans-Butene [% by mass] | 18–21 | 18–21 | 7–10 | 7–10 | 11–13 | 11–13 |
| 1-Butene [% by mass] | 35–45 | 35–45 | 15–35 | 15–35 | 11–13 | 11–13 |
| Isobutene [% by mass] | 22–28 | 22–28 | 33–50 | 33–50 | 14–16 | 14–16 |
| cis-Butene [% by mass] | 5–9 | 5–9 | 4–8 | 4–8 | 10–12 | 10–12 |
| 1,3-Butadiene [ppmw] | 500–8000 | 0–50 | 50–8000 | 0–50 | <10000 | 0–50 |

Explanation
$HCC_4$: typical of a $C_4$ mixture which is obtained from the crack-$C_4$ of a steamcracker (high severity) after the hydrogenation of the 1,3-butadiene without additional moderation of the catalyst.
$HCC_4$/SHP: $HCC_4$ composition in which residues of 1,3-butadiene have been reduced further in an SHP.
Raff. I (raffinate I): typical of a $C_4$ mixture which is obtained from the crack-$C_4$ of a steamcracker (high severity) after the removal of the 1,3-butadiene, for example by an NMP extractive rectification.
Raff. I/SHP: Raff. I composition in which residues of 1,3-butadiene have been reduced further in an SHP.
$CC_4$: typical composition of a crack-$C_4$ which is obtained from a catcracker.
$CC_4$/SHP: $CC_4$ composition in which residues of 1,3-butadiene have been reduced further in an SHP.

Among others, the raffinate I or $HCC_4$ is an isobutenic hydrocarbon mixture used with preference in the ETBE process. Because plants for working up $C_4$ hydrocarbons are generally constructed as a strand (integrated system of a plurality of plants), it is, however, possible that the raffinate I or $HCC_4$ passes through one or more other process stage(s) before entry into the ETBE process. This process stage or these process stages may, for example, also be a process or process step(s) as have been described in the embodiments for process step a). $C_4$ hydrocarbon mixtures usable in the ETBE process may also be those as obtained from processes as per the embodiments of process step a) and subsequent separation as per process step b). In particular, those mixtures as obtained in the preparation of tert-butanol (TBA) from isobutene after removal of the TBA may also be used. In this way, an individually adapted overall concept for workup with the appropriate product portfolio can be realized in each case.

Typical processes which can be connected upstream of the ETBE processes are water scrubbings, purification processes in adsorbers, drying processes, and distillations.

Water Scrubbing (ETBE Process)

A water scrubbing can fully or partly remove hydrophilic components, for example, nitrogen components, from the technical hydrocarbon mixture containing isobutene and linear butenes to be used. Examples of nitrogen components are acetonitrile or n-methylpyirolidone (which can stem, for example, from a 1,3-butadiene extractive distillation). Oxygen compounds (for example, acetone from FCC) may also be removed partly by means of a water scrubbing. After a water scrubbing, the isobutenic hydrocarbon stream is saturated with water. In order to avoid biphasicity in the downstream process steps in the reactor, the reaction temperature there should be approx. 10° C. above the temperature of the water scrubbing.

Adsorber (ETBE Process)

Adsorbers are used to remove impurities. This removal may be advantageous, for example, when noble metal catalysts are used in one of the process steps. Often, nitrogen or sulfur compounds are removed by means of upstream adsorbers. Examples of adsorbents are aluminas, molecular sieves, zeolites, activated carbon, aluminas impregnated with metals. Adsorbents are sold by various companies, for example Alcoa (Selexsorb®).

Drying (ETBE Process)

Any water present in the isobutenic hydrocarbon mixture, which may stem, for example, from the water scrubbing, can be removed by known processes for drying. Suitable processes are, for example, the distillative removal of the water as an azeotrope. Often, an azeotrope containing $C_4$ hydrocarbons may be utilized or azeotroping agents may be added.

The drying of the hydrocarbon mixture may be advantageous for various reasons, for example, to reduce the formation of alcohols (mainly tert-butyl alcohol) in step a) or to avoid technical problems as a result of separation of water or to prevent ice formation at low temperatures (for example, in the course of intermediate storage).

Distillation (ETBE Process)

Distillation steps may be utilized, for example, to remove impurities (for example, low boilers such as $C_3$ hydrocarbons, high boilers such as $C_5$ hydrocarbons) or to obtain fractions with different isobutene concentrations. This removal can be done either directly with the raffinate I or the $HCC_4$ or after one or more other process stage(s) has/have been passed through. Direct distillation of the raffinate I or of the $HCC_4$ makes it possible, for example, to separate into a relatively isobutene-rich fraction depleted in 2-butenes and n-butane.

Depending on the composition of the technical hydrocarbon mixture to be used and/or on the purities of the target products, the technical hydrocarbon mixture may thus be used directly in step a) of the preferred ETBE process or else only after a pretreatment by one or more of the aforementioned processes.

The preferred ETBE process can be used in a simple manner to prepare ETBE or a composition that contains ETBE and is obtained as the bottom product of the reactive distillations or of the distillations in steps b) and e), preferably as the bottom product of step b).

The present invention therefore also in particular provides a process for preparing ETBE, in particular the process just described for preparing ETBE, which is characterized in that relatively low-water ethanol prepared by the process according to the invention for preparing relatively low-water ethanol is used as a reactant in the ETBE process and that excess ethanol from the ETBE process and fresh ethanol are fed as water-rich ethanol streams with different water content to the process according to the invention for preparing relatively low-water ethanol.

The process according to the invention is illustrated in detail with reference to FIG. 1 to FIG. 3 by block connection diagrams, without any intention that the process be restricted to the embodiments depicted there by way of example. In the schematic illustrations, only the essential stages are shown. The illustration of streams customary in process technology, for example, cooling water streams, circulation streams or feedback streams, and/or customary apparatus has been dispensed with partly in favor of better clarity. Common components, for example, pumps, vacuum pumps, valves, heat exchangers, which are not shown in the block connection diagrams may, however, be components in a plant for performing the process according to the invention.

A block diagram of a process variant with which the dewatering of the ethanol streams can be carried out by the process according to the invention is shown in FIG. 1. The ethanol (4) with the relatively high water content is introduced into the membrane unit (5). There, a retentate (6) that has the specified water content and a water-rich permeate (3*b*) are obtained. The relatively low-water ethanol stream (1) is introduced into the membrane unit (2). The retentate (7) obtained is ethanol with the desired water content and a permeate (3*a*). The retentates (6) and (7) are combined to a common stream (76) which can preferably be used in an ETBE plant, for example, as a reactant in the etherification reactors. The permeates (3*a*) and (3*b*) may be worked up separately or preferably together. One possibility consists in the distillative separation into water and into a top product that comprises either the ethanol/water azeotrope or the ethanol/water azeotrope and additional water. The distillate may be recycled into the dewatering plant at a suitable point, for example, as stream (4) or as a portion of stream (4).

Figure 2:
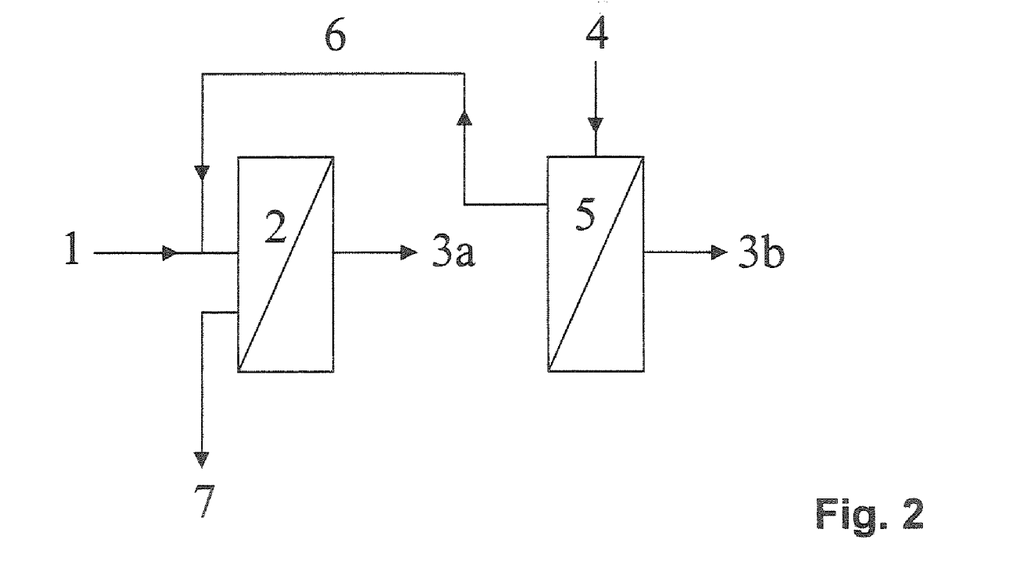
FIG. 2 is a block diagram showing another embodiment of the invention.

A block diagram of a second process variant with which the dewatering of the ethanol streams by the process according to the invention can be carried out is shown in FIG. 2. The ethanol (4) having the relatively high water content is introduced into the membrane unit (5). There, a retentate (6) that has virtually the same water content as the ethanol stream (1), and a water-rich permeate (3*b*) are formed. The relatively low-water ethanol stream (1) is introduced together with retentate (6) into the membrane unit (2). The retentate (7) obtained is ethanol with the desired water content and a permeate (3*a*). The retentate (7) is preferably used as a reactant in an ETBE synthesis. The permeates (3*a*) and (3*b*) may be worked up separately or preferably together. One possibility consists in the distillative separation into water and into a top product that comprises either the ethanol/water azeotrope or the ethanol/water azeotrope and additional water. The distillate may be recycled into the dewatering plant at a suitable point, for example, as stream (4) or as a portion thereof.

Figure 3:
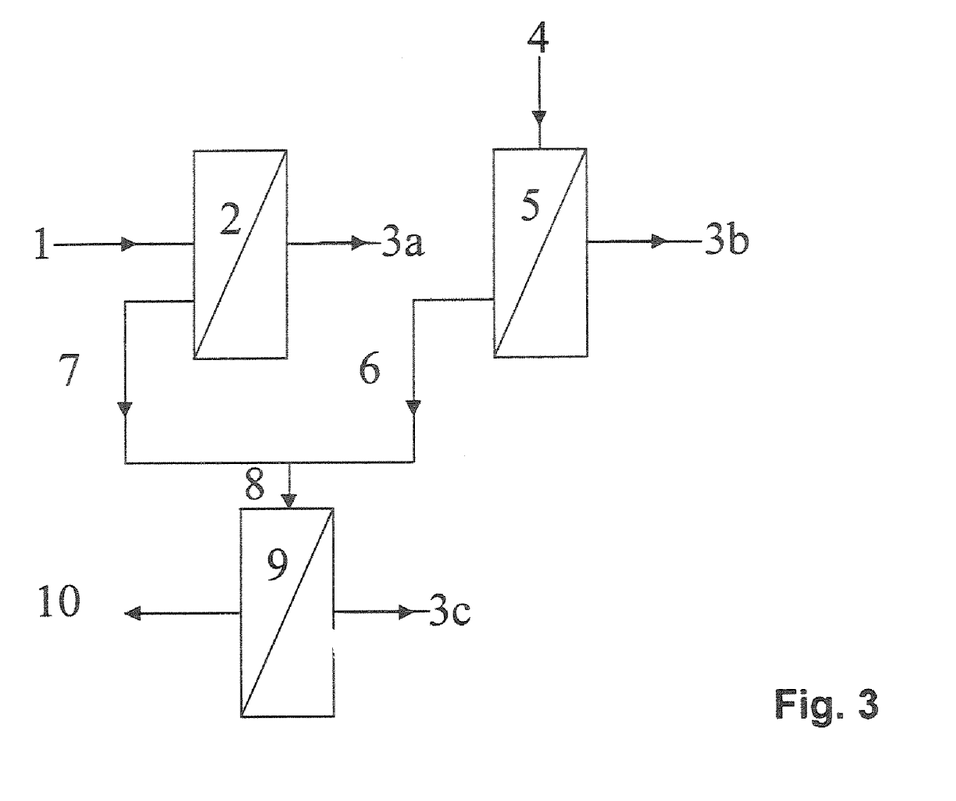
FIG. 3 is a block diagram showing a third embodiment of the invention.

A block diagram of a further process variant is shown by FIG. 3. In the membrane unit (2), the ethanol stream (1) is separated into a relatively low-water retentate (7) and into a water-rich permeate (3*a*). In the membrane unit (5), the ethanol stream (4) is separated into a retentate (6) that has virtually the same water content as retentate (7), and a water-rich permeate (3b). The retentates (7) and (6) are separated together in membrane unit (9) into an ethanol stream (10) with the desired water content and into a water-rich permeate (3c). The ethanol stream (10) is preferably used in an ETBE plant. The permeates (3a), (3b) and (3c) may be worked up separately or preferably together. One possibility consists in the distillative separation into water and into a top product that comprises either the ethanol/water azeotrope or the ethanol/water azeotrope and additional water. The distillate may be recycled into the dewatering plant at a suitable point, for example, as stream (4) or a portion thereof.

The examples that follow are intended to illustrate the invention without restricting the scope of protection that is evident from the patent claims and the description.

EXAMPLES

To illustrate the advantages of the inventive connections, two examples are shown. Two streams are to be dried, as can occur in industrial processes, in particular in ETBE preparation:

A fresh ethanol stream of 10 t/h with a water content of 1% by mass.

A return ethanol stream of 1.45 t/h with a water content of 9% by mass.

The target is a residual concentration of 0.3% by mass of water in the dried ethanol.

The operating temperature was 90° C. A polyvinyl alcohol (PVA) membrane common for ethanol drying was used. For this membrane type, comprehensive test data have been published in the literature (S. Klatt: Zum Einsatz der Pervaporation im Umfeld der chemischen Industries, Shaker Verlag 1993; M. Franke: Auslegung und Optimierung von Pervaporationsanlagen zur Entwässerung von Lösungsmitteln und Lösungsmittelgemischen, thesis, Aachen, 1990). At 90° C., these membranes attain a pure water flow rate of about 14 kg/m² h (Klatt, 1993). Commercial PVA membranes are freely available under trade names such as PERVAP 2200 (Sulzer Chemtech), for example.

According to Brüschke (Brüschke, H. E. A.: State of Art of Pervaporation Processes, In: Nunes, S. P. and Peinemann, K.-V. (Eds.): Membrane Technology in the chemical Industry, Wiley-VCH, 2001), the membrane surface area was calculated by the equation:

$$A = \dot{m}\frac{1}{J_0}\ln\left(\frac{C_{Feed}}{C_{Product}}\right)$$

In this equation, A was the desired membrane surface area in m², $\dot{m}$ was the feed mass flow rate in kg/h, $J_0$ was the extrapolated pure water flow rate in kg/(m²h), and $C_{Feed}$ and $C_{Product}$ were the concentration of the feed and of the retentate in % by mass. The selectivity of the customary dewatering membranes is constant over wide concentration ranges and did not have to be taken into account for a comparative investigation in which similar concentration ranges are passed through in all variants. Selectivities for the PERVAP 2200 dewatering membrane are reported, for example, by Brüschke (2001). The permeate workup (condensation and vacuum unit) was not considered further in the examples calculated.

As Example 1 (comparison), a noninventive process is calculated in which the two feed streams (1) and (4) are mixed upstream of the membrane unit. This gives rise to a mean feed concentration of 2.01% by mass and a required membrane surface area calculated by the abovementioned formula of 1557 m².

As Example 2, an inventive process according to FIG. 2 is calculated, in which the return ethanol (4) is dried in a dedicated membrane unit (5) down to a water content of 1% by mass. To this end, about 352 m² of membrane surface area are required. Subsequently, the retentate (6) is mixed with the fresh ethanol (1) and fed to a second membrane unit (2) in which the overall stream attains the water specification of 0.3% by mass. For the second membrane unit, a membrane surface area of about 860 m² is then determined. In total, the unit in Example 2 has a surface area of 1212 m². For the two membrane units (2) and (5), the permeate is worked up together.

The results of Examples 1 and 2 are summarized in Table 2. A comparison of the two examples directly allows one to assess the advantages of the process according to the invention. A large part of the operating costs of a membrane unit is caused by regular membrane replacement after expiry of lifetime. As a result of the process, in membrane units, the other operating costs such as heating output, equipment for the vacuum unit and the permeate workup too are, at a first approximation, proportional to the membrane surface area. At a total of about 1212 m², the membrane surface area in the process according to the invention is approx. 22% smaller than in the comparative unit described in Example 1. This gives rise to the following advantages (see also Table 2):

In Example 2, the capital costs are approx. 18% below those of the unit according to Example 1.

In Example 2, the operating costs are approx. 22% below those of the unit according to Example 1.

TABLE 2

Results of the calculations for Example 1 and Example 2

| | Stream | Feed rate [kg/h] | Water content in feed [% by ma.] | Water content in product [% by ma.] | Membrane surface area [m²] | Relative membrane surface area [%] | Capital costs [%] | Operating costs [%] |
|---|---|---|---|---|---|---|---|---|
| Example 1 (comparison) | Streams (1) and (4) | 11450 | 2.0 | 0.3 | 1557 | 100.0 | 100.0 | 100.0 |

TABLE 2-continued

Results of the calculations for Example 1 and Example 2

|  | Stream | Feed rate [kg/h] | Water content in feed [% by ma.] | Water content in product [% by ma.] | Membrane surface area [m²] | Relative membrane surface area [%] | Capital costs [%] | Operating costs [%] |
|---|---|---|---|---|---|---|---|---|
| Example 2 (FIG. 1) | Streams (1) | 10000 | 1.0 | 0.3 | 860 | | | |
|  | Stream (4) | 1450 | 9.0 | 0.3 | 352 | | | |
|  | Total | 11450 | | | 1212 | 77.9 | 82.0 | 78.0 |

The invention claimed is:

1. A process for preparing relatively low-water ethanol from at least two streams of relatively water-rich ethanol that have a different water content, the process comprising
introducing separately the ethanol streams with different water contents into different membrane units in which the ethanol streams are each separated into relatively low-water ethanol as the retentate and relatively water-rich permeate, and
combining the retentate stream from at least one membrane unit for separating an ethanol stream with a relatively high water content with the feed stream and/or the retentate stream of at least one other membrane unit for separating an ethanol stream, wherein only streams that have a difference in ethanol concentration of not more than 1% by mass absolute are combined.

2. A process according to claim 1, wherein the dewatering at the membrane is carried out at a temperature of from 20 to 150° C.

3. A process according to claim 1, wherein the dewatering at the membrane is carried out with a pressure difference of from 0.001 to 2 MPa.

4. A process according to claim 1, wherein the water removal at the membrane is effected by reverse osmosis, pervaporation or vapor permeation.

5. A process according to claim 1, wherein a pressure difference is generated by generating a vacuum on the permeate side of the membrane.

6. A process according to claim 5, wherein the pressure difference is generated by generating a reduced pressure on the permeate side of all membranes used by means of a common reduced-pressure unit.

7. A process according to claim 1, wherein at least one stream of relatively low-water ethanol which has a water content of below 1% by mass is obtained.

8. A process according to claim 1, wherein two relatively water-rich ethanol streams with different water contents, whose water concentrations differ by more than 1.0% by mass, are used.

9. A process according to claim 1, wherein at least one relatively water-rich ethanol stream is fresh alcohol and at least one relatively water-rich ethanol stream stems from an ETBE plant.

10. A process according to claim 1, wherein the water-rich permeates obtained in the dewatering in the membrane units are worked up separately.

11. A process according to claim 1, wherein the water-rich permeates obtained in the dewatering in the membrane units are worked up together.

12. A process according to claim 10, wherein the permeate is separated by distillation into water and at least one distillate consisting of an ethanol/water mixture, and the distillate is recycled into a membrane unit as a relatively water-rich ethanol stream.

13. A process according to claim 10, wherein the permeate, together with an ethanolic aqueous extract from an ETBE plant, is worked up by distillation, and the ethanol-rich distillate is recycled into a membrane unit as a relatively water-rich ethanol stream.

14. A process according to claim 1, wherein the retentates, when their water concentrations differ by less than 0.2% by mass, are combined.

15. A process according to claim 1, wherein two or more retentate streams are combined and are dewatered in a further membrane unit.

16. A process according to claim 1, wherein the retentate stream from the membrane unit for separating an ethanol stream with a relatively high water content is combined with the feed stream of a membrane unit for separating an ethanol stream with a relatively low water content.

17. A process according to claim 1, wherein the relatively low-water ethanol prepared in accordance with the invention is used as a reactant in an ETBE synthesis and the excess ethanol from the process of ETBE synthesis is removed by extraction with water from the ETBE process, and this extraction stream is fed, directly or after a distillative workup, as a water-rich ethanol stream to a membrane unit.

* * * * *